United States Patent [19]
Guskey

[11] Patent Number: 5,977,036
[45] Date of Patent: *Nov. 2, 1999

[54] STYLING SHAMPOO COMPOSITIONS

[75] Inventor: Susan Marie Guskey, Montgomery, Ohio

[73] Assignee: The Procter & Gamble Company, Cincinnati, Ohio

[*] Notice: This patent issued on a continued prosecution application filed under 37 CFR 1.53(d), and is subject to the twenty year patent term provisions of 35 U.S.C. 154(a)(2).

[21] Appl. No.: 09/017,596

[22] Filed: Feb. 3, 1998

[51] Int. Cl.⁶ ............................ A61K 7/075; A61K 7/11
[52] U.S. Cl. ..................... 510/121; 510/122; 510/123; 510/124; 510/125; 510/127; 510/128; 510/466; 510/475; 424/70.1; 424/70.11; 424/70.12; 424/70.15; 424/70.16; 424/70.19; 424/70.21; 424/70.24; 424/70.28; 424/70.31
[58] Field of Search ................................ 510/119, 121, 510/122, 123, 124, 125, 127, 128, 466, 475; 424/70.1, 70.11, 70.12, 70.15, 70.16, 70.19, 70.21, 70.24, 70.28, 70.31

[56] References Cited

U.S. PATENT DOCUMENTS 5,221,530  6/1993  Janchitraponvej et al. .............. 424/70
5,573,709  11/1996  Wells ........................................ 510/122
5,658,557  8/1997  Bolich, Jr. et al. .................. 424/70.12
5,716,920  2/1998  Glenn, Jr. et al. ...................... 510/259

*Primary Examiner*—Margaret Einsmann
*Attorney, Agent, or Firm*—Stephen T. Murphy; Tara M. Rosnell; William J. Winter

[57] ABSTRACT

Disclosed are hair styling shampoo compositions which comprise from about 5% to about 50% by weight of a surfactant selected from the group consisting of anionic surfactants, zwitterionic or amphoteric surfactants having an attached group that is anionic at the pH of the composition, and combinations thereof; from about 0.025% to about 3% by weight of an organic cationic polymer having a cationic charge density of from about 0.2 meq/gm to about 7 meq/gm and a molecular weight of from about 5,000 to about 10 million; from about 0.1% to about 10% by weight of a water-insoluble hair styling polymer; from about 0.1% to about 10% by weight of a water-insoluble volatile solvent; and from about 0.005% to about 2.0% by weight a crystalline hydroxyl-containing stabilizing agent; and from about 26.5% to about 94.9% by weight water. The composition provides improved spreading efficiency of the styling polymer onto hair, thus providing improved styling performance from the shampoo composition.

28 Claims, No Drawings

STYLING SHAMPOO COMPOSITIONS

FIELD OF THE INVENTION

The present invention relates to hair styling shampoo compositions which provide improved styling performance. More particularly, the present invention relates to styling shampoo compositions which contain a water insoluble hair styling polymer, water insoluble carrier for the hair styling polymer, a cationic deposition polymer and select stability agents to improve the styling performance and the feel of the hair.

BACKGROUND OF THE INVENTION

Many hair shampoo compositions provide acceptable cleaning but provide little or no styling benefits, e.g. body, hold, stiffness. To realize such benefits, separate cleaning and styling products are often used.

Recently, hair shampoo compositions have been developed which can provide cleaning and styling performance from a single product. Many of these products contain styling polymers in a compatible shampoo base. To prepare such products, styling polymers can be dissolved in an organic solvent and then incorporated into the shampoo base. The organic solvent thereafter helps disperse the styling polymer in the shampoo composition, and also helps enhance spreading of the styling polymer onto hair such that the polymer sets and forms welds between hair fibers. The enhanced spreading of the styling polymer onto the hair results in improved styling performance from the shampoo composition.

Another method for further improving polymer deposition from a shampoo involves the use of cationic deposition polymers. These cationic deposition polymers improve the deposition efficiency of the styling polymers, which in turn also improves styling performance. The improved deposition from the cationic polymer can also allow for reduction of the amount of styling polymer formulated into the shampoo composition, thus reducing raw material costs. Cationic deposition polymers, however, can cause compatibility problems with other materials in the formulation, especially when used at higher concentrations or at relatively high cationic charge densities. Moreover, excessive amounts of such deposition polymers can result in undesirably coated or oily wet hair feel, and can cause the hair when dry to feel dirty and have less body, less fullness.

It has now been found that these water-insoluble styling polymers in volatile carriers can be rendered more effective, and the build-up issues associated with cationic deposition polymers can be avoided, when these components are used in combination with select stabilizers. It is believed that the select stabilizers enhance the deposition efficiency of the hair styling polymer over conventional stabilizers, allowing for more formulation freedom to either lower the cationic deposition polymer usage level, or to incorporate new cationic deposition polymers with improved build-up profiles. Moreover, incorporation of these select stabilizers results in significant improvements to the hair feel while delivering the desired styling polymer deposit morphology, or character, to the hair for optimal style achievement performance from the styling shampoo.

In view of the foregoing, it is therefore an object of the present invention to provide a styling shampoo composition with improved styling performance. It is a further object of the present invention to improve the storage stability of the styling shampoo and the feel of the hair after repeated use of the styling shampoo by using select stabilizing agents in combination with a water-insoluble styling polymer, a volatile carrier for the styling polymer, and a cationic deposition polymer.

SUMMARY OF THE INVENTION

The present invention is directed to hair styling shampoo compositions which comprise from about 5% to about 50% by weight of a surfactant selected from the group consisting of anionic surfactants, zwitterionic or amphoteric surfactants, and combinations thereof; from about 0.025% to about 3% by weight of an organic cationic polymer having a cationic charge density of from about 0.2 meq/gm to about 7 meq/gm and a molecular weight of from about 5,000 to about 10 million; from about 0.1% to about 10% by weight of a water-insoluble hair styling polymer; from about 0.1% to about 10% by weight of volatile water insoluble solvent which is a carrier for the styling polymer previously having a boiling point of less than about 300° C. and a water solubility at 25° C. of preferably less than about 0.2% by weight; and from about 0.005% to about 2.0% by weight of a crystalline hydroxyl-containing stabilizing agent; and from about 25.0% to about 94.8% by weight of water.

It has been found that the shampoo composition of the present invention provides improved styling performance coupled with improved feel of the hair after styling relative to previous styling shampoo compositions. It has also been found that the select stabilizing agent, when used in combination with the cationic deposition polymer, water-insoluble styling polymer, water-insoluble volatile carrier for the styling polymer, surfactant, and water, provides for enhanced deposition efficiency of the styling polymer over conventional stabilizers without being limited by theory, it is believed that these select stabilizers can be used at significantly lower levels than conventional stabilizers to achieve storage stability. Additionally, less of the stabilizer is solubilized into the surfactant micelle, thus resulting in less interference with coacervate formation between the cationic deposition polymer and the surfactants. As a result, less cationic deposition polymer is required to achieve the desired styling polymer deposition level and the resulting coacervate delivers conditioned feel to the hair without an unacceptable coated character and without build-up after repeated usage of the styling shampoo.

DETAILED DESCRIPTION OF THE INVENTION

The shampoo compositions of the present invention can comprise, consist of, or consist essentially of the essential elements and limitations of the invention described herein, as well any of the additional or optional ingredients, components, or limitations described herein.

As used herein, the term "water-insoluble" refers to any material that has a solubility in water at 25° C. of less than about 0.5%, preferably less than about 0.3%, even more preferably less than about 0.2% by weight.

All percentages, parts and ratios are based on the total weight of the shampoo compositions of the present invention, unless otherwise specified. All such weights as they pertain to listed ingredients are based on the active level and, therefore, do not include carriers or by-products that may be included in commercially available materials, unless otherwise specified.

The styling shampoo compositions of the present invention, including the essential and some optional components thereof, are described in detail hereinafter.

Detersive Surfactant Component

The styling shampoo compositions of the present invention comprise an detersive surfactant component to provide cleaning performance to the composition. The detersive surfactant component in turn comprises anionic detersive surfactant, zwitterionic or amphoteric detersive surfactant, or a combination thereof. Such surfactants should be physically and chemically compatible with the essential components described herein, or should not otherwise unduly impair product stability, aesthetics or performance.

Suitable anionic detersive surfactant components for use in the shampoo composition herein include those which are known for use in hair care or other personal care cleansing compositions. The concentration of the anionic surfactant component in the shampoo composition should be sufficient to provide the desired cleaning and lather performance, and generally range from about 5% to about 50%, preferably from about 8% to about 30%, more preferably from about 10% to about 25%, even more preferably from about 12% to about 22%, by weight of the composition.

Preferred anionic surfactants suitable for use in the shampoo compositions are the alkyl and alkyl ether sulfates. These materials have the respective formulae $ROSO_3M$ and $RO(C_2H_4O)_xSO_3M$, wherein R is alkyl or alkenyl of from about 8 to about 18 carbon atoms, x is an integer having a value of from 1 to 10, and M is a cation such as ammonium, alkanolamines, such as triethanolamine, monovalent metals, such as sodium and potassium, and polyvalent metal cations, such as magnesium, and calcium. Solubility of the surfactant will depend upon the particular anionic detersive surfactants and cations chosen.

Preferably, R has from about 8 to about 18 carbon atoms, more preferably from about 10 to about 16 carbon atoms, even more preferably from about 12 to about 14 carbon atoms, in both the alkyl and alkyl ether sulfates. The alkyl ether sulfates are typically made as condensation products of ethylene oxide and monohydric alcohols having from about 8 to about 24 carbon atoms. The alcohols can be synthetic or they can be derived from fats, e.g., coconut oil, palm kernel oil, tallow. Lauryl alcohol and straight chain alcohols derived from coconut oil or palm kernel oil are preferred. Such alcohols are reacted with between about 0 and about 10, preferably from about 2 to about 5, more preferably about 3, molar proportions of ethylene oxide, and the resulting mixture of molecular species having, for example, an average of 3 moles of ethylene oxide per mole of alcohol, is sulfated and neutralized.

Specific non limiting examples of alkyl ether sulfates which may be used in the shampoo compositions of the present invention include sodium and ammonium salts of coconut alkyl triethylene glycol ether sulfate, tallow alkyl triethylene glycol ether sulfate, and tallow alkyl hexaoxyethylene sulfate. Highly preferred alkyl ether sulfates are those comprising a mixture of individual compounds, wherein the compounds in the mixture have an average alkyl chain length of from about 10 to about 16 carbon atoms and an average degree of ethoxylation of from about 1 to about 4 moles of ethylene oxide.

Other suitable anionic detersive surfactants are the water-soluble salts of organic, sulfuric acid reaction products conforming to the formula $[R^1—SO_3—M]$ where $R^1$ is a straight or branched chain, saturated, aliphatic hydrocarbon radical having from about 8 to about 24, preferably about 10 to about 18, carbon atoms; and M is a cation described hereinbefore. Non limiting examples of such detersive surfactants are the salts of an organic sulfuric acid reaction product of a hydrocarbon of the methane series, including iso-, neo, and n-paraffins, having from about 8 to about 24 carbon atoms, preferably about 12 to about 18 carbon atoms and a sulfonating agent, e.g., $SO_3$, $H_2SO_4$, obtained according to known sulfonation methods, including bleaching and hydrolysis. Preferred are alkali metal and ammonium sulfonated $C_{10}$ to $C_{18}$ n-paraffins.

Still other suitable anionic detersive surfactants are the reaction products of fatty acids esterified with isethionic acid and neutralized with sodium hydroxide where, for example, the fatty acids are derived from coconut oil or palm kernel oil; sodium or potassium salts of fatty acid amides of methyl tauride in which the fatty acids, for example, are derived from coconut oil or palm kernel oil. Other similar anionic surfactants are described in U.S. Pat. Nos. 2,486,921; 2,486,922; and 2,396,278, which descriptions are incorporated herein by reference.

Other anionic detersive surfactants suitable for use in the shampoo compositions are the succinnates, examples of which include disodium N-octadecylsulfosuccinnate; disodium lauryl sulfosuccinate; diammonium lauryl sulfosuccinate; tetrasodium N-(1,2-dicarboxyethyl)-N-octadecylsulfosuccinnate; diamyl ester of sodium sulfosuccinic acid; dihexyl ester of sodium sulfosuccinic acid; and dioctyl esters of sodium sulfosuccinic acid.

Other suitable anionic detersive surfactants include olefin sulfonates having about 10 to about 24 carbon atoms. In this context, the term "olefin sulfonates" refers to compounds which can be produced by the sulfonation of alpha-olefins by means of uncomplexed sulfur trioxide, followed by neutralization of the acid reaction mixture in conditions such that any sulfones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form. The alpha-olefins from which the olefin sulfonates are derived are mono-olefins having from about 10 to about 24 carbon atoms, preferably from about 12 to about 16 carbon atoms. Preferably, they are straight chain olefins. In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. A non limiting example of such an alpha-olefin sulfonate mixture is described in U.S. Pat. No. 3,332,880, which description is incorporated herein by reference.

Another class of anionic detersive surfactants suitable for use in the shampoo compositions are the beta-alkyloxy alkane sulfonates. These surfactants conform to the formula

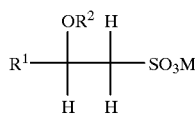

where $R^1$ is a straight chain alkyl group having from about 6 to about 20 carbon atoms, $R^2$ is a lower alkyl group having from about 1 to about 3 carbon atoms, preferably 1 carbon atom, and M is a water-soluble cation as described hereinbefore.

Preferred anionic detersive surfactants for use in the shampoo compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, and combinations thereof.

Suitable amphoteric or zwitterionic detersive surfactants for use in the shampoo composition herein include those which are known for use in hair care or other personal care cleansing. Concentration of such amphoteric detersive surfactants preferably ranges from about 0.5% to about 20%, preferably from about 1% to about 10%, by weight of the composition. Non limiting examples of suitable zwitterionic or amphoteric surfactants are described in U.S. Pat. Nos. 5,104,646 (Bolich Jr. et al.), 5,106,609 (Bolich Jr. et al.), which descriptions are incorporated herein by reference.

Amphoteric detersive surfactants suitable for use in the shampoo composition are well known in the art, and include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group such as carboxy, sulfonate, sulfate, phosphate, or phosphonate. Preferred amphoteric detersive surfactants for use in the present invention include cocoamphoacetate, cocoamphodiacetate, lauroamphoacetate, lauroamphodiacetate, and mixtures thereof.

Zwitterionic detersive surfactants suitable for use in the shampoo composition are well known in the art, and include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Zwitterionics such as betaines are preferred.

The shampoo compositions of the present invention may further comprise additional surfactants for use in combination with the anionic detersive surfactant component described hereinbefore. Suitable optional surfactants include nonionic surfactants. Any such surfactant known in the art for use in hair or personal care products may be used, provided that the optional additional surfactant is also chemically and physically compatible with the essential components of the shampoo composition, or does not otherwise unduly impair product performance, aesthetics or stability. The concentration of the optional additional surfactants in the shampoo composition may vary with the cleansing or lather performance desired, the optional surfactant selected, the desired product concentration, the presence of other components in the composition, and other factors well known in the art.

Non limiting examples of other anionic, zwitterionic, amphoteric or optional additional surfactants suitable for use in the shampoo compositions are described in McCutcheon's, Emulsifiers and Detergents, 1989 Annual, published by M. C. Publishing Co., and U.S. Pat. Nos. 3,929,678, 2,658,072; 2,438,091; 2,528,378, which descriptions are incorporated herein by reference.

Cationic Deposition Polymer

The shampoo compositions of the present invention comprise an organic cationic polymer as a deposition aid for the styling polymer component described hereinafter. The concentration of the cationic polymer in the shampoo composition ranges from about 0.025% to about 3%, preferably from about 0.05% to about 0.5%, more preferably from about 0.1% to about 0.25%, by weight of the shampoo composition.

The cationic polymer for use in the shampoo composition of the present invention contains cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the styling shampoo composition. The average molecular weight of the cationic polymer is between about 10 million and about 5,000, preferably at least about 100,000, more preferably at least about 200,000, but preferably not more than about 2 million, more preferably not more than about 1.5 million. The polymers also have a cationic charge density ranging from about 0.2 meq/gm to about 7 meq/gm, preferably at least about 0.4 meq/gm, more preferably at least about 0.6 meq/gm, but also preferably less than about 5 meq/gm, more preferably less than about 2 meq/gm, at the pH of intended use of the shampoo composition, which pH will generally range from about pH 3 to about pH 9, preferably between about pH 4 and about pH 7.

Any anionic counterions can be use in association with the cationic polymers so long as the polymers remain soluble in water, in the shampoo composition, or in a coacervate phase of the shampoo composition, and so long as the counterions are physically and chemically compatible with the essential components of the shampoo composition or do not otherwise unduly impair product performance, stability or aesthetics. Non limiting examples of such counterions include halides (e.g., chlorine, fluorine, bromine, iodine), sulfate and methylsulfate.

The cationic nitrogen-containing moiety of the cationic polymer is generally present as a substituent on all, or more typically on some, of the monomer units thereof. Thus, the cationic polymer for use in the shampoo composition includes homopolymers, copolymers, terpolymers, and so forth, of quaternary ammonium or cationic amine-substituted monomer units, optionally in combination with non-cationic monomers referred to herein as spacer monomers. Non limiting examples of such polymers are described in the CTFA Cosmetic Ingredient Dictionary, 3rd edition, edited by Estrin, Crosley, and Haynes, (The Cosmetic, Toiletry, and Fragrance Association, Inc., Washington, D.C. (1982)), which description is incorporated herein by reference.

Non limiting examples of suitable cationic polymers include copolymers of vinyl monomers having cationic protonated amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone or vinyl pyrrolidone. The alkyl and dialkyl substituted monomers preferably have from $C_1$ to $C_7$ alkyl groups, more preferably from $C_1$ to $C_3$ alkyl groups. Other suitable spacer monomers include vinyl esters, vinyl alcohol (made by hydrolysis of polyvinyl acetate), maleic anhydride, propylene glycol, and ethylene glycol.

Suitable cationic protonated amino and quaternary ammonium monomers, for inclusion in the cationic polymers of the shampoo composition herein, include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are preferably lower alkyls such as the $C_1$, $C_2$ or $C_3$ alkyls.

Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably $C_1$–$C_7$ hydrocarbyls, more preferably $C_1$–$C_3$ alkyls.

Other suitable cationic polymers for use in the shampoo composition include copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16), such as those commercially available from BASF Wyandotte Corp. (Parsippany, N.J., U.S.A.) under the LUVIQUAT tradename (e.g., LUVIQUAT FC 370); copolymers of 1-vinyl-2-pyrrolidone and dimethylaminoethyl methacrylate (referred to in the industry by CTFA as Polyquaternium-11) such as those commercially available from ISP Corporation (Wayne, N.J., U.S.A.) under the GAFQUAT tradename (e.g., GAFQUAT 755N); cationic diallyl quaternary ammonium-containing polymers, including, for example, dimethyldiallylammonium chloride homopolymer and copolymers of acrylamide and dimethyldiallylammonium chloride, referred to in the industry (CTFA) as Polyquaternium 6 and Polyquaternium 7, respectively; and mineral acid salts of amino-alkyl esters of homopolymers and copolymers of unsaturated carboxylic acids having from 3 to 5 carbon atoms, as described in U.S. Pat. No. 4,009,256, which description is incorporated herein by reference.

Other suitable cationic polymers for use in the shampoo composition include polysaccharide polymers, such as cationic cellulose derivatives and cationic starch derivatives. Suitable cationic polysaccharide polymers include those which conform to the formula

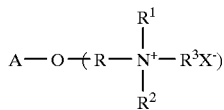

wherein A is an anhydroglucose residual group, such as a starch or cellulose anhydroglucose residual; R is an alkylene oxyalkylene, polyoxyalkylene, or hydroxyalkylene group, or combination thereof; R1, R2, and R3 independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in R1, R2 and R3) preferably being about 20 or less; and X is an anionic counterion as described in hereinbefore.

Preferred cationic cellulose polymers are those polymers available from Amerchol Corp. (Edison, N.J., USA) in their Polymer JR and LR series of polymers, as salts of hydroxyethyl cellulose reacted with trimethyl ammonium substituted epoxide, referred to in the industry (CTFA) as Polyquaternium 10. Another type of preferred cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the trade name Polymer LM-200.

Other suitable cationic polymers include cationic guar gum derivatives, such as guar hydroxypropyltrimonium chloride, specific examples of which include the Jaguar series commercially available from Rhone-Poulenc Incorporated. Other suitable cationic polymers include quaternary nitrogen-containing cellulose ethers, some examples of which are described in U.S. Pat. No. 3,962,418, which description is incorporated herein by reference herein. Other suitable cationic polymers include copolymers of etherified cellulose, guar and starch, some examples of which are described in U.S. Pat. No. 3,958,581, which description is incorporated herein by reference.

The cationic polymers herein are either soluble in the shampoo composition, or preferably are soluble in a complex coacervate phase in the shampoo composition formed by the cationic polymer and the anionic detersive surfactant component described hereinbefore. Complex coacervates of the cationic polymer can also be formed with other charged materials in the shampoo composition.

Coacervate formation is dependent upon a variety of criteria such as molecular weight, component concentration, and ratio of interacting ionic components, ionic strength (including modification of ionic strength, for example, by addition of salts), charge density of the cationic and anionic components, pH, and temperature. Coacervate systems and the effect of these parameters have been described, for example, by J. Caelles, et al., "Anionic and Cationic Compounds in Mixed Systems", *Cosmetics & Toiletries,* Vol. 106, April 1991, pp 49–54, C. J. van Oss, "Coacervation, Complex-Coacervation and Flocculation", *J. Dispersion Science and Technology,* Vol. 9 (5,6), 1988–89, pp 561–573, and D. J. Burgess, "Practical Analysis of Complex Coacervate Systems", *J. of Colloid and Interface Science,* Vol. 140, No. 1, November 1990, pp 227–238, which descriptions are incorporated herein by reference.

It is believed to be particularly advantageous for the cationic polymer to be present in the shampoo composition in a coacervate phase, or to form a coacervate phase upon application or rinsing of the shampoo to or from the hair. Complex coacervates are believed to more readily deposit on the hair. Thus, in general, it is preferred that the cationic polymer exist in the shampoo composition as a coacervate phase or form a coacervate phase upon dilution. If not already a coacervate in the shampoo composition, the cationic polymer will preferably exist in a complex coacervate form in the shampoo upon dilution with water.

Techniques for analysis of formation of complex coacervates are known in the art. For example, microscopic analyses of the shampoo compositions, at any chosen stage of dilution, can be utilized to identify whether a coacervate phase has formed. Such coacervate phase will be identifiable as an additional emulsified phase in the composition. The use of dyes can aid in distinguishing the coacervate phase from other insoluble phases dispersed in the shampoo composition.

Styling Polymer

The shampoo compositions of the present invention comprise a water-insoluble hair styling polymer, concentrations of which range from about 0.1% to about 10%, preferably from about 0.3% to about 7%, more preferably from about 0.5% to about 5%, by weight of the composition. These styling polymers provide the shampoo composition of the present invention with hair styling performance by providing polymeric deposits on the hair after application from a shampoo composition. The polymer deposited on the hair has adhesive and cohesive strength and delivers styling primarily by forming welds between hair fibers upon drying, as is understood by those skilled in the art.

Many such polymers are known in the art, including water-insoluble organic polymers and water-insoluble silicone-grafted polymers, all of which are suitable for use in the shampoo composition herein provided that they also have the requisite features or characteristics described hereinafter. Such polymers can be made by conventional or otherwise known polymerization techniques well known in the art, an example of which includes free radical polymerization.

Examples of suitable organic and silicone grafted polymers for use in the shampoo composition of the present invention are described in greater detail hereinafter.

I. Organic styling polymer

The hair styling polymers suitable for use in the shampoo composition of the present invention include organic hair styling polymers well known in the art. The organic styling polymers may be homopolymers, copolymers, terpolymers or other higher polymers, but must comprise one or more polymerizable hydrophobic monomers to thus render the resulting styling polymer hydrophobic and water-insoluble as defined herein. The styling polymers may therefore further comprise other water soluble, hydrophillic monomers provided that the resulting styling polymers have the requisite hydrophobicity and water insolubility.

As used herein, the term "hydrophobic monomer" refers to polymerizable organic monomers that can form with like monomers a water-insoluble homopolymer, and the term "hydrophilic monomer" refers to polymerizable organic monomers that can form with like monomers a water-soluble homopolymer.

The organic styling polymers preferably have a weight average molecular weight of at least about 20,000, preferably greater than about 25,000, more preferably greater than about 30,000, most preferably greater than about 35,000. There is no upper limit for molecular weight except that which limits applicability of the invention for practical reasons, such as processing, aesthetic characteristics, formulateability, etc. In general, the weight average molecular weight will be less than about 10,000,000, more generally less than about 5,000,000, and typically less than about 2,000,000. Preferably, the weight average molecular weight will be between about 20,000 and about 2,000,000, more preferably between about 30,000 and about 1,000,000, and most preferably between about 40,000 and about 500,000.

The organic styling polymers also preferably have a glass transition temperature (Tg) or crystalline melting point (Tm) of at least about −20° C., preferably from about 20° C. to about 80° C., more preferably from about 20° C. to about 60° C. Styling polymers having these Tg or Tm values form styling films on hair that are not unduly sticky or tacky to the touch. As used herein, the abbreviation "Tg" refers to the glass transition temperature of the backbone of the polymer, and the abbreviation "Tm" refers to the crystalline melting point of the backbone, if such a transition exists for a given polymer. Preferably, both the Tg and the Tm, if any, are within the ranges recited hereinabove.

The organic styling polymers are carbon chains derived from polymerization of hydrophobic monomers such as ethylenically unsaturated monomers, cellulosic chains or other carbohydrate-derived polymeric chains. The backbone may comprise ether groups, ester groups, amide groups, urethanes, combinations thereof, and the like.

The organic styling polymers may further comprise one or more hydrophilic monomers in combination with the hydrophobic monomers described herein, provided that the resulting styling polymer has the requisite hydrophobic character and water-insolubility. Suitable hydrophilic monomers include, but are not limited to, acrylic acid, methacrylic acid, N,N-dimethylacrylamide, dimethyl aminoethyl methacrylate, quaternized dimethylaminoethyl methacrylate, methacrylamide, N-t-butyl acrylamide, maleic acid, maleic anhydride and its half esters, crotonic acid, itaconic acid, acrylamide, acrylate alcohols, hydroxyethyl methacrylate, diallyldimethyl ammonium chloride, vinyl pyrrolidone, vinyl ethers (such as methyl vinyl ether), maleimides, vinyl pyridine, vinyl imidazole, other polar vinyl heterocyclics, styrene sulfonate, allyl alcohol, vinyl alcohol (such as that produced by the hydrolysis of vinyl acetate after polymerization), salts of any acids and amines listed above, and mixtures thereof. Preferred hydrophillic monomers include acrylic acid, N,N-dimethyl acrylamide, dimethylaminoethyl methacrylate, quaternized dimethyl aminoethyl methacrylate, vinyl pyrrolidone, salts of acids and amines listed above, and combinations thereof.

Suitable hydrophobic monomers for use in the organic styling polymer include, but are not limited to, acrylic or methacrylic acid esters of $C_1$–$C_{18}$ alcohols, such as methanol, ethanol, methoxy ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol(2-methyl-2-propanol), cyclohexanol, neodecanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-tri methyl-1-hexanol, 1-decanol, 1-dodecanol, 1-hexadecanol, 1-octa decanol, and the like, the alcohols having from about 1 to about 18 carbon atoms, preferably from about 1 to about 12 carbon atoms; styrene; polystyrene macromer; vinyl acetate; vinyl chloride; vinylidene chloride; vinyl propionate; alpha-methylstyrene; t-butylstyrene; butadiene; cyclohexadiene; ethylene; propylene; vinyl toluene t-butylethacrylate; and mixtures thereof. Preferred hydrophobic monomers include n-butyl methacrylate, isobutyl methacrylate, t-butyl acrylate, t-butyl methacrylate t-butylethacrylate, 2-ethylhexyl methacrylate, methyl methacrylate, vinyl acetate, and mixtures thereof, more preferably t-butyl acrylate, t-butyl methacrylate, or combinations thereof The styling polymers for use in the shampoo composition preferably comprise from about 20% to 100%, more preferably from about 50% to about 100%, even more preferably from about 60% to about 100%, by weight of the hydrophobic monomers, and may further comprise from zero to about 80% by weight of hydrophilic monomers. The particular selection and combination of monomers for incorporation into the styling polymer will help determine its formulational properties. By appropriate selection and combination of, for example, hydrophilic and hydrophobic monomers, the styling polymer can be optimized for physical and chemical compatibility with the selected styling polymer solvent described hereinafter and other components of the shampoo composition. The selected monomer composition of the organic styling polymer must, however, render the styling polymer water-insoluble but soluble in the selected styling polymer solvent described hereinafter. In this context, the organic styling polymer is soluble in the styling polymer solvent if the organic polymer is solubilized in the solvent at 25° C. at the polymer and solvent concentrations of the shampoo formulation selected. However, a solution of the organic styling polymer and styling polymer solvent may be heated to speed up solubility of the styling polymer in the styling polymer solvent. Such styling polymer and solvent formulation, including the selection of monomers for use in the styling polymer, to achieve the desired solubility is well within the skill of one in the art.

Examples of preferred organic styling polymers include t-butyl acrylate/2-ethylhexyl acrylate copolymers having a weight/weight ratio of monomers of about 95/5, about 90/10, about 80/20, about 70/30, about 60/40, and about 50/50; t-butyl acrylate/2-ethylhexyl methacrylate copolymers having a weight/weight ratio of monomers of about 95/5, about 90/10, about 80/20, about 70/30, about 60/40, and about 50/50; t-butyl methacrylate/2-ethylhexyl acrylate copolymers having a weight/weight ratio of monomers of about 95/5, about 90/10, about 80/20, about 70/30, about 60/40, and about 50/50; t-butyl methacrylate/2-ethylhexyl methacrylate copolymers having a weight/weight ratio of monomers of about 95/5, about 90/10, about 80/20, about 70/30, about 60/40, and about 50/50; t-butyl ethacrylate/2-ethylhexyl methacrylate copolymers having a weight/weight ratio of monomers of about 95/5, about 90/10, about 80/20, about 70/30, about 60/40, and about 50/50; vinyl pyrrolidone/vinyl acetate copolymers having a weight/weight ratio of monomers of about 10/90, and about 5/95; and mixtures thereof.

Especially preferred polymers are t-butyl acrylate/2-ethylhexyl methacrylate copolymers having a weight/weight ratio of monomers of about 95/5, about 90/10, about 80/20, about 70/30, about 60/40, and about 50/50; t-butyl methacrylate/2-ethylhexyl methacrylate copolymers having a weight/weight ratio of monomers of about 95/5, about 90/10, about 80/20, about 70/30, about 60/40, and about 50/50; and mixtures thereof.

Examples of other suitable styling polymers are described in U.S. Pat. Nos. 5,120,531, to Wells et al., issued Jun. 9, 1992; 5,120,532, to Wells et al., issued Jun. 9, 1992; 5,104,642, to Wells et al., issued Apr. 14, 1992; 4,272,511, to Papantoniou et al., issued Jun. 9, 1981; 5,672,576, to Behrens et al., issued Sep. 30, 1997; and 4,196,190, to Gehman et al., issued Apr. 1, 1980, which descriptions are incorporated herein by reference.

II. Silicone-grafted styling Polymer

Other suitable styling polymers for use in the shampoo composition of the present invention are silicone-grafted hair styling resins. These polymers may be used alone or in combination with the organic styling polymers described hereinbefore. Many such polymers suitable for use in the shampoo composition herein are known in the art. These polymers are characterized by polysiloxane moieties covalently bonded to and pendant from a polymeric carbon-based backbone.

The backbone of the silicone-grafted polymer is preferably a carbon chain derived from polymerization of ethylenically unsaturated monomers, but can also be cellulosic chains or other carbohydrate-derived polymeric chains to which polysiloxane moieties are pendant. The backbone can also include ether groups, ester groups, amide groups, urethane groups and the like. The polysiloxane moieties can be substituted on the polymer or can be made by co-polymerization of polysiloxane-containing polymerizable monomers (e.g. ethylenically unsaturated monomers, ethers, and/or epoxides) with non-polysiloxane-containing polymerizable monomers.

The silicone-grafted styling polymers for use in the shampoo composition comprise "silicone-containing" (or "polysiloxane-containing") monomers, which form the silicone macromer pendant from the backbone, and non-silicone-containing monomers, which form the organic backbone of the polymer.

Preferred silicone-grafted polymers comprise an organic backbone, preferably a carbon backbone derived from ethylenically unsaturated monomers, such as a vinyl polymeric backbone, and a polysiloxane macromer (especially preferred are polydialkylsiloxane, most preferably polydimethylsiloxane) grafted to the backbone. The polysiloxane macromer should have a weight average molecular weight of at least about 500, preferably from about 1,000 to about 100,000, more preferably from about 2,000 to about 50,000, most preferably about 5,000 to about 20,000. Organic backbones contemplated include those that are derived from polymerizable, ethylenically unsaturated monomers, including vinyl monomers, and other condensation monomers (e.g., those that polymerize to form polyamides and polyesters), ring-opening monomers (e.g., ethyl oxazoline and caprolactone), etc. Also contemplated are backbones based on cellulosic chains, ether-containing backbones, etc.

Preferred silicone grafted polymers for use in the shampoo composition comprise monomer units derived from: at least one free radically polymerizable ethylenically unsaturated monomer or monomers and at least one free radically polymerizable polysiloxane-containing ethylenically unsaturated monomer or monomers.

The silicone grafted polymers suitable for use in the shampoo composition generally comprise from about 1% to about 50%, by weight, of polysiloxane-containing monomer units and from about 50% to about 99% by weight, of non-polysiloxane-containing monomers. The non-polysiloxane-containing monomer units can be derived from the hydrophilic and/or hydrophobic monomer units described hereinbefore.

The styling polymer for use in the shampoo composition can therefore comprise combinations of the hydrophobic and/or polysiloxane-containing monomer units described herein, with or without hydrophilic comonomers as described herein, provided that the resulting styling polymer has the requisite characteristics as described herein.

Suitable polymerizable polysiloxane-containing monomers include, but are not limited to, those monomers that conform to the formula:

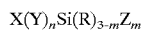

$$X(Y)_n Si(R)_{3-m} Z_m$$

wherein X is an ethylenically unsaturated group copolymerizable with the hydrophobic monomers described herein, such as a vinyl group; Y is a divalent linking group; R is a hydrogen, hydroxyl, lower alkyl (e.g. $C_1$–$C_4$), aryl, alkaryl, alkoxy, or alkylamino; Z is a monovalent siloxane polymeric moiety having a number average molecular weight of at least about 500, which is essentially unreactive under copolymerization conditions, and is pendant from the vinyl polymeric backbone described above; n is 0 or 1; and m is an integer from 1 to 3. These polymerizable polysiloxane-containing monomers have a weight average molecular weight as described above.

A preferred polysiloxane-containing monomer conforms to the formula:

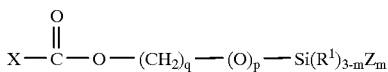

wherein m is 1, 2 or 3 (preferably m=1); p is 0 or 1; q is an integer from 2 to 6; $R^1$ is hydrogen, hydroxyl, lower alkyl, alkoxy, alkylamino, aryl, or alkaryl (preferably $R^1$ is alkyl); X conforms to the formula

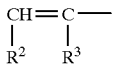

wherein $R^2$ is hydrogen or —COOH (preferably $R^2$ is hydrogen); $R^3$ is hydrogen, methyl or —CH$_2$COOH (preferably $R^3$ is methyl); Z conforms to the formula:

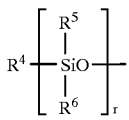

wherein $R^4$, $R^5$, and $R^6$ independently are lower alkyl, alkoxy, alkylamino, aryl, arylalkyl, hydrogen or hydroxyl (preferably $R^4$, $R^5$, and $R^6$ are alkyls); and r is an integer of about 5 or higher, preferably about 10 to about 1500 (most preferably r is from about 100 to about 250). Most preferably, $R^4$, $R^5$, and $R^6$ are methyl, p=0, and q=3.

Another preferred polysiloxane monomer conforms to either of the following formulas

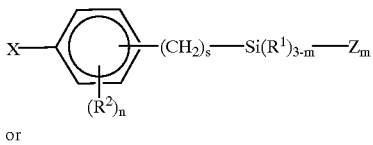

wherein: s is an integer from 0 to about 6, preferably 0, 1, or 2, more preferably 0 or 1; m is an integer from 1 to 3, preferably 1; $R^2$ is C1–C10 alkyl or C7–C10 alkylaryl, preferably C1–C6 alkyl or C7–C10 alkylaryl, more preferably C1–C2 alkyl; n is an integer from 0 to 4, preferably 0 or 1, more preferably 0.

The silicone grafted styling polymers suitable for use in the shampoo composition preferably comprise from about 50% to about 99%, more preferably from about 60% to about 98%, most preferably from about 75% to about 95%, by weight of the polymer, of non-silicone macromer-containing monomer units, e.g. the total hydrophobic and hydrophilic monomer units described herein, and from about 1% to about 50%, preferably from about 2% to about 40%, more preferably from about 5% to about 25%, of silicone macromer-containing monomer units, e.g. the polysiloxane-containing monomer units described herein. The level of hydrophilic monomer units can be from about 0% to about 70%, preferably from about 0% to about 50%, more preferably from about 0% to about 30%, most preferably from about 0% to about 15%; the level of hydrophobic monomer units, can be from 30% to about 99%, preferably from about 50% to about 98%, more preferably from about 70% to about 95%, most preferably from about 85% to about 95%.

Examples of some suitable silicone grafted polymers for use in the shampoo composition herein are listed below. Each listed polymer is followed by its monomer composition as weight part of monomer used in the synthesis:

(i) t-butylacrylatye/t-butyl-methacrylate/2-ethylhexyl-methacrylate/PDMS macromer—20,000 molecular weight macromer 31/27/32/10

(ii) t-butylmethacrylate/2-ethylhexyl-methacrylate/PDMS macromer—15,000 molecular weight macromer 75/10/15

(iii) t-butylmethacrylate/2-ethylhexyl-acrylate/PDMS macromer—10,000 molecular weight macromer 65/15/20

(iv) t-butylacrylate/2-ethylhexyl-acrylate/PDMS macromer—14,000 molecular weight macromer 77/11/12

(v) t-butylacrylate/2-ethylhexyl-methacrylate/PDMS macromer—13,000 molecular weight macromer 81/9/10

Examples of other suitable silicone grafted polymers for use in the shampoo composition of the present invention are described in EPO Application 90307528.1, published as EPO Application 0 408 311 A2 on Jan. 11, 1991, Hayama, et al.; U.S. Pat. Nos. 5,061,481, issued Oct. 29, 1991, Suzuki et al.; 5,106,609, Bolich et al., issued Apr. 21, 1992; 5,100,658, Bolich et al., issued Mar. 31, 1992; 5,100,657, Ansher-Jackson, et al., issued Mar. 31, 1992; 5,104,646, Bolich et al., issued Apr. 14, 1992; U.S. Ser. No. 07/758,319, Bolich et al, filed Aug. 27, 1991, U.S. Ser. No. 07/758,320, Torgerson et al., filed Aug. 27, 1991, which descriptions are incorporated herein by reference.

Volatile Carrier for the Styling Polymer

The shampoo composition of the present invention comprises a volatile carrier for solubilizing the hair styling polymers described hereinbefore. The carrier helps disperse the hair styling polymer as water-insoluble fluid particles throughout the shampoo composition, wherein the dispersed particles comprise the styling polymer and the volatile carrier. Carriers suitable for this purpose include hydrocarbons, ethers, esters, amines, alkyl alcohols, volatile silicone derivatives and combinations thereof, many examples of which are well known in the art.

The volatile carrier must be water-insoluble or have a low water solubility. The selected styling polymer, however, must also be sufficiently soluble in the selected carrier to allow dispersion of the hair styling polymer and solvent combination as a separate, dispersed fluid phase in the shampoo composition.

The carrier for use in the shampoo composition must also be a volatile material. In this context, the term volatile means that the carrier has a boiling point of less than about 300° C., preferably from about 90° C. to about 260° C., more preferably from about 100° C. to about 200° C. (at about one atmosphere of pressure).

The concentration of the volatile carrier in the shampoo composition must be sufficient to solubilize the hair styling polymer and disperse it as a separate fluid phase in the shampoo composition. Such concentrations generally range from about 0.10% to about 10%, preferably from about 0.5% to about 8%, most preferably from about 1% to about 6%, by weight of the shampoo composition, wherein the weight ratio of styling polymer to carrier is preferably from about 10:90 to about 70:30, more preferably from about 20:80 to about 65:35, even more preferably from about 30:70 to about 60:40. If the weight ratio of styling polymer to carrier is too low, the lathering performance of the shampoo composition is negatively affected. If the ratio of polymer to solvent is too high, the composition becomes too viscous and causes difficulty in the dispersion of the styling polymer. The hair styling agents should have an average particle diameter in the final shampoo product of from about 0.05 to about 100 microns, preferably from about 1 to about 25 microns, more preferably from about 0.5 to about 10 microns. Particle size can be measured according to methods known in the art, including, for example optical microscopy.

Preferred volatile carriers for use in the shampoo composition are the hydrocarbon solvents, especially branched chain hydrocarbon solvents. The hydrocarbon solvents may be linear or branched, saturated or unsaturated, hydrocarbons having from about 8 to about 18 carbon atoms, preferably from about 10 to about 16 carbon atoms. Saturated hydrocarbons are preferred, as are branched hydrocarbons. Nonlimiting examples of some suitable linear hydrocarbons include decane, dodecane, decene, tridecene, and combinations thereof. Suitable branched hydrocarbons include isoparaffins, examples of which include commercially available isoparaffins from Exxon Chemical Company such as Isopar H and K ($C_{11}$–$C_{12}$ isoparaffins), and Isopar L ($C_{11}$–$C_{13}$ isoparaffins). Preferred branched hydrocarbons are isohexadecane, isododecane, 2,5-dimethyl decane, isotetradecane, and combinations thereof. Commercially available branched hydrocarbons include Permethyl 99A and 101A (available from Preperse, Inc., South Plainfield, N.J., USA).

Other suitable carriers include isopropanol, butyl alcohol, amyl alcohol, phenyl ethanol, benzyl alcohol, phenyl propanol, ethyl butyrate, isopropyl butyrate, diethyl phthalate, diethyl malonate, diethyl succinate, dimethyl malonate, dimethyl succinate, phenyl ethyl dimethyl carbinol, ethyl-6-acetoxyhexanoate, and methyl (2-pentanyl-3-oxy)cyclopentylacetate, and mixtures thereof. Preferred among such other suitable solvents are diethyl phthalate, diethyl malonate, diethyl succinate, dimethyl malonate, dimethyl succinate, phenylethyl dimethyl carbinol, ethyl-6-acetoxyhexanoate, and mixtures thereof.

Suitable ether carriers are the di($C_5$–$C_7$) alkyl ethers and diethers, especially the di($C_5$–$C_6$) alkyl ethers such as isoamyl ether, dipentyl ether and dihexyl ether.

Other suitable carriers for use in the shampoo composition the volatile silicon derivatives such as cyclic or linear polydialkylsiloxane, linear siloxy compounds or silane. The number of silicon atoms in the cyclic silicones is preferably from about 3 to about 7, more preferably about 3 to about 5.

The general formula for such silicones is:

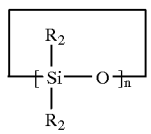

wherein $R_1$ and $R_2$ are independently selected from $C_1$ to $C_8$ alkyl, aryl or alkylaryl and wherein n=3–7. The linear polyorgano siloxanes have from about 2 to 7 silicon atoms and have the general formula:

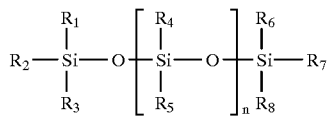

wherein $R_1$, $R_2$, $R_3$, $R_4$, $R_5$, $R_6$, $R_7$ and $R_8$ can independently be saturated or unsaturated $C_1$–$C_8$ alkyl, aryl, alkylaryl, hydroxyalkyl, amino alkyl or alkyl siloxy.

Linear siloxy compounds have the general formula:

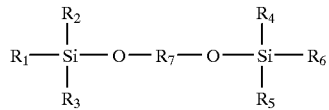

wherein $R_1$, $R_2$, $R_3$, $R_4$, $R_5$, and $R_6$ are independently selected from saturated or unsaturated $C_1$ to $C_7$ alkyl, aryl and alkyl aryl and $R_7$ is $C_1$ to $C_4$ alkylene.

Silane compounds have the general formula:

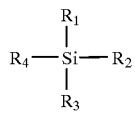

wherein $R_1$, $R_2$, $R_3$, and $R_4$ can independently be selected from $C_1$–$C_8$ alkyl, aryl, alkylaryl, hydroxyalkyl and alkylsiloxy.

Silicones of the above type, both cyclic and linear, are offered by Dow Coming Corporation, Dow Corning 344, 345 and 200 fluids, Union Carbide, Silicone 7202 and Silicone 7158, and Stauffer Chemical, SWS-03314.

The linear volatile silicones generally have viscosities of less than about 5 centistokes at 25° C. while the cyclic materials have viscosities less than about 10 centistokes. Examples of volatile silicones are described in Todd and Byers, "Volatile Silicone Fluids for Cosmetics", Cosmetics and Toiletries, Vol. 91, January, 1976, pp. 27–32, and also in Silicon Compounds, pages 253–295, distributed by Petrarch Chemicals, which descriptions are incorporated herein by reference.

Select Stability Active

The shampoo compositions of the present invention comprise a select crystalline, hydroxyl-containing stabilizer. The stabilizer is used to form a crystalline stabilizing network in the emulsion that prevents the styling polymer/volatile carrier droplets from coalescing and the shampoo from phase splitting. Additionally, significantly lower levels of the crystalline, hydroxyl-containing stabilizer need to be used relative to traditional stability actives. This results in enhanced deposition efficiency of the hair styling polymer onto the hair as well as reduced interactions with other shampoo components.

The stabilizers used herein are not surfactants. The stabilizers provide improved shelf and stress stability, but allow the styling polymer/volatile carrier emulsion to separate upon lathering, and thereby provide for increased styling polymer deposition onto the hair.

The stabilizer suitable for use in the shampoo compositions are characterized by the general formula:

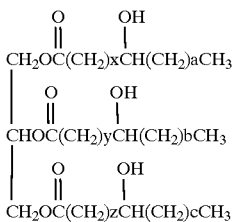

wherein:
 (x+a) is from between 11 and 17,
 (y+b) is from between 11 and 17,
 (z+c) is from between 11 and 17;
preferably:
 x=y=z–10, and
 a=b=c=5.

The crystalline, hydroxyl-containing stabilizer comprises from about 0.005% to about 2.0%, preferably from about 0.05% to about 0.25% by weight of the composition. The preferred suspending agent for use in the compositions herein is trihydroxstearin available from Rheox, Inc. (New Jersey, USA) under the tradename Thixcin R.

Optional Components

The shampoo compositions of the present invention may further comprise one or more optional components known for use in hair care or personal care products, provided that the optional components are physically and chemically compatible with the essential components described herein, or do not otherwise unduly impair product stability, aesthetics or performance. Individual concentrations of such optional components may range from about 0.001% to about 10% by weight of the shampoo compositions.

Non limiting examples of optional components for use in the shampoo composition include anti dandruff agents, conditioning agents (hydrocarbon oils, fatty esters, silicones) dyes, nonvolatile solvents or diluents (water soluble and insoluble), pearlescent aids, foam boosters, additional surfactants or nonionic cosurfactants, pediculocides, pH adjusting agents, perfumes, preservatives, proteins, skin active agents, sunscreens, vitamins, and viscosity adjusting agents.

The shampoo composition of the present invention preferably further comprises select cationic materials which act as spreading agents for the styling polymer/volatile carrier droplets. These optional cationic spreading agents are described in more detail hereinafter.

The shampoo composition of the present invention also preferably comprises select polyalkylene glycols to enhance hair feel and enhance styling performance. These optional polyalkylene glycols are described in more detail hereinafter.

The shampoo composition of the present invention also preferably comprises a silicone hair conditioning agent to enhance hair feel, especially the soft, silky feel of dry hair. These optional silicone hair conditioning agents are described in more detail hereinafter.

The shampoo composition of the present invention also preferably comprises additional optional agents which improve the performance and/or aesthetics of the composition. These materials impact which shampoo components are solubilized by the surfactant component and how much of each component is solubilized, influencing coacervate formation and composition. These additional agents are also entrapped in the coacervate, thus impacting styling performance and hair feel both directly and indirectly. These additional optional agents are described in more detail hereinafter.

Cationic Spreading Agent

The shampoo compositions of the present invention may further comprise select cationic materials which act as spreading agents. The spreading agents for use in the composition are select quaternary ammonium or protonated amino compounds defined in greater detail hereinafter. These select spreading agents are useful to enhance the morphology of the styling polymer deposit on the hair so that more efficient adhesion between hair fibers results in improved styling performance. The concentration of the select spreading agents in the composition range from about 0.05% to about 5%, preferably from about 0.1% to about 2%, more preferably from about 0.5% to about 1.5%, by weight of the shampoo composition.

The select spreading agents are quaternary ammonium or amino compounds having 2, 3 or 4 N-radicals which are substituted or unsubstituted hydrocarbon chains having from about 12 to about 30 carbon atoms, wherein the substituents includes nonionic hydrophilic moieties selected from alkoxy, polyoxalkylene, alkylamido, hydroxyalkyl, alkylester moieties, and mixtures thereof. Suitable hydrophile-containing radicals include, for example, compounds having nonionic hydrophile moieties selected from the group consisting of ethoxy, propoxy, polyoxyethylene, polyoxypropylene, ethylamido, propylamido, hydroxymethyl, hydroxyethyl, hydroxypropyl, methylester, ethylester, propylester, or mixtures thereof. The select spreading agents are cationic and must be positively charged at the pH of the shampoo compositions. Generally, the pH of the shampoo composition will be less than about 10, typically from about 3 to about 9, preferably from about 4 to about 8.

Select cationic spreading agents for use in the composition include those corresponding to the formula:

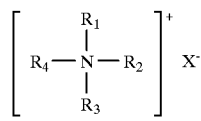

wherein $R_1$, and $R_2$ are independently a saturated or unsaturated, substituted or unsubstituted, linear or branched hydrocarbon chain having from about 12 to about 30 carbon atoms, preferably from about 18 to about 22 carbon atoms, and wherein the hydrocarbon chain can contain one or more hydophilic moieties selected from the alkoxy, polyoxyalkylene, alkylamido, hydroxyalkyl, alkylester, and mixtures thereof; $R_3$ and $R_4$ are independently a hydrogen, or a saturated or unsaturated, substituted or unsubstituted, linear or branched hydrocarbon chain having from about 1 to about 30 carbon atoms, or a hydrocarbon having from about 1 to about 30 carbon atoms containing one or more aromatic, ester, ether, amido, amino moieties present as substitutents or as linkages in the chain, and wherein the hydrocarbon chain can contain one or more hydophilic moieties selected from the alkoxy, polyoxyalkylene, alkylamido, hydroxyalkyl, alkylester, and mixtures thereof; and X is a soluble salt forming anion preferably selected from halogen (especially chlorine), acetate, phosphate, nitrate, sulfonate, and alkylsulfate radicals.

An example of a select spreading agent for use in the composition include those corresponding to the formula:

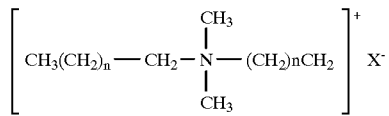

wherein n is from 10–28, preferably 16, and X is a water soluble salt forming anion (e.g., Cl, sulfate, etc.)

Other examples of select cationic spreading agents for use in the composition include those corresponding to the formula:

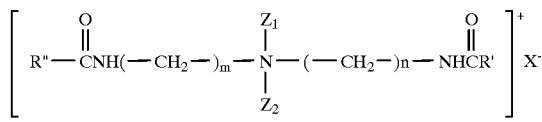

wherein $Z_1$ and $Z_2$ are independently saturated or unsaturated, substituted or unsubstituted, linear or branched hydrocarbons, and preferably $Z_1$ is an alkyl, more preferably methyl, and $Z_2$ is a short chain hydroxyalkyl, preferably hydroxymethyl or hydroxyethyl; n and m are independently integers from 1 to 4, inclusive, preferably from 2 to 3, inclusive, more preferably 2; R' and R" are independently substituted or unsubstituted hydrocarbons, preferably $C_{12}$–$C_{20}$ alkyl or alkenyl; and X is a soluble salt forming anion (e.g., Cl, sulfate, etc.).

Nonlimiting examples of suitable cationic spreading agents include ditallowdimethyl ammonium chloride, ditallowdimethyl ammonium methyl sulfate, dihexadecyl dimethyl ammonium chloride, di-(hydrogenated tallow) dimethyl ammonium chloride, dioctadecyl dimethyl ammonium chloride, dieicosyl dimethyl ammonium chloride, didocosyl dimethyl ammonium chloride, di-(hydrogenated tallow) dimethyl ammonium acetate, dihexadecyl dimethyl ammonium acetate, ditallow dipropyl ammonium phosphate, ditallow dimethyl ammonium nitrate, di-(coconutalkyl) dimethyl ammonium chloride, ditallowamidoethyl hydroxypropylmonium methosulfate (commercially available as Varisoft 238), dihydrogenated tallowamidoethyl hydroxyethylmonium methosulfate (commercially available as Varisoft 110), ditallowamidoethyl hydroxyethylmonium methosulfate (commercially available as Varisoft 222), and di(partially hardened soyoylethyl) hydroxyethylmonium methosulfate (commercially available as Armocare EQ-S). Ditallowdimethyl ammonium chloride, ditallowamidoethyl hydroxypropylmonium methosulfate, dihydrogenated tallowamidoethyl hydroxyethylmonium methosulfate, ditallowamidoethyl hydroxyethylmonium methosulfate, and di(partially hardened soyoylethyl) hydroxyethylmonium methosulfate are particularly preferred quaternary ammonium cationic surfactants useful herein.

Other suitable quaternary ammonium cationic surfactants are described in M.C. Publishing Co., *McCutcheion's Detergents & Emulsifiers,* (North American edition 1979); Schwartz, et al., *Surface Active Agents. Their Chemistry and Technology,* New York: Interscience Publishers, 1949; U.S. Pat. Nos. 3,155,591, to Hilfer, issued Nov. 3, 1964; 3,929,678 to Laughlin et al., issued Dec. 30, 1975; 3,959,461 to Bailey et al, issued May 25, 1976; and 4,387,090 to Bolich Jr., issued Jun. 7, 1983, which descriptions are incorporated herein by reference.

Polyalkylene Glycol

The shampoo compositions of the present invention may further comprise selected polyalkylene glycols in amounts effective to enhance the conditioned feel of the hair, to mitigate the coated hair feel resulting from the cationic deposition polymer, and to enhance the styling performance of the shampoo. Effective concentrations of the selected polyethylene glycols range from about 0.025% to about 1.5%, preferably from about 0.05% to about 1.0%, more preferably from about 0.1% to about 0.5%, by weight of the shampoo composition.

The polyalkylene glycols suitable for use in the shampoo compositions are characterized by the general formula:

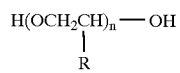

wherein R is hydrogen, methyl or mixtures thereof, preferably hydrogen, and n is an integer having an average value of from about 1,500 to about 25,000, preferably from about 2,500 to about 20,000, and more preferably from about 3,500 to about 15,000. When R is hydrogen, these materials are polymers of ethylene oxide, which are also known as polyethylene oxides, polyoxyethylenes, and polyethylene glycols. When R is methyl, these materials are polymers of propylene oxide, which are also known as polypropylene oxides, polyoxypropylenes, and polypropylene glycols. When R is methyl, it is also understood that various positional isomers of the resulting polymers can exist.

Specific examples of suitable polyethylene glycol polymers include PEG-14 M wherein R is hydrogen and n has an average value of about 14,000 (PEG-14 M is also known as Polyox WSR® N-3000 available from Union Carbide) and PEG-23 M wherein R is hydrogen and n has an average value of about 23,000 (PEG-23 M is also known as Polyox WSR® N-12K available from Union Carbide).

Suitable polyalkylene polymers include polypropylene glycols and mixed polyethylene/ polypropylene glycols.

It has been found that these polyalkylene glycols, when added to the styling shampoo compositions described herein, enhance the conditioned hair feel by mitigating the coated hair feel resulting from deposition of the cationic deposition polymer. Moreover, these polyalkene glycols also significantly enhance the styling performance versus compositions formulated without polyethylene glycols. This performance is especially surprising as polyalkene glycols are not known to deliver any styling performance to hair and a synergistic relationship with the other styling shampoo components could not be anticipated.

Silicone Hair Conditioning Agent

The shampoo compositions of the present invention may further comprise an optional silicone hair conditioning agent at concentrations effective to provide hair conditioning benefits. Such concentrations range from about 0.01% to about 10%, preferably from about 0.1% to about 8%, more preferably from about 0.1% to about 5%, most preferably from about 0.2% to about 3%, by weight of the shampoo compositions.

The optional silicone hair conditioning agents are insoluble in the shampoo compositions, and are preferably nonvolatile. Typically it will be intermixed in the shampoo composition so as to be in the form of a separate, discontinuous phase of dispersed, insoluble particles, also referred to as droplets. The optional silicone hair conditioning agent phase will comprise a silicone fluid hair conditioning agent such as a silicone fluid and can also comprise other ingredients, such as a silicone resin to improve silicone fluid deposition efficiency or enhance glossiness of the hair (especially when high refractive index (e.g. above about 1.46) silicone conditioning agents are used (e.g. highly phenylated silicones).

The optional silicone hair conditioning agent phase may comprise volatile silicone, nonvolatile silicone, or combinations thereof. Typically, if volatile silicones are present, it will be incidental to their use as a solvent or carrier for commercially available forms of nonvolatile silicone materials ingredients, such as silicone gums and resins.

The optional silicone hair conditioning agents for use in the shampoo compositions preferably have a viscosity of from about 20 to about 2,000,000 centistokes, more preferably from about 1,000 to about 1,800,000 centistokes, even more preferably from about 50,000 to about 1,500,000 centistokes, as measured at 25° C.

Optional silicone fluids include silicone oils which are flowable silicone materials having a a viscosity of less than 1,000,000 centistokes, preferably between about 5 and 1,000,000 centistokes, more preferably between about 10 and about 100,000 centistokes, at 25° C. Suitable silicone oils include polyalkyl siloxanes, polyaryl siloxanes, polyalkylaryl siloxanes, polyether siloxane copolymers, and combinations thereof Other insoluble, nonvolatile silicone fluids having hair conditioning properties can also be used.

Optional silicone oils include polyalkyl or polyaryl siloxanes which conform to the following formula (I)

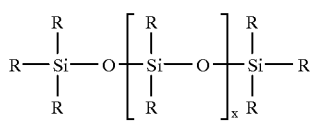

where R is aliphatic, preferably alkyl or alkenyl, or aryl, R can be substituted or unsubstituted, and x is an integer from 1 to about 8,000. Suitable unsubstituted R groups include alkoxy, aryloxy, alkaryl, arylalkyl, arylalkenyl, alkylamine, and ether-substituted, hydroxyl-substituted, and halogen-substituted aliphatic and aryl groups. Suitable R groups also include cationic amines and quaternary ammonium groups.

The aliphatic or aryl groups substituted on the siloxane chain may have any structure so long as the resulting silicones remain fluid at room temperature, are hydrophobic, are neither irritating, toxic nor otherwise harmful when applied to the hair, are compatible with the other components of the shampoo compositions, are chemically stable under normal use and storage conditions, are insoluble in the shampoo compositions herein, and are capable of being deposited on and conditioning the hair.

The two R groups on the silicon atom of each monomeric silicone unit may represent the same or different groups. Preferably, the two R groups represent the same group.

Preferred alkyl and alkenyl substituents are $C_1$–$C_5$ alkyls and alkenyls, more preferably from $C_1$–$C_4$, most preferably from $C_1$–$C_2$. The aliphatic portions of other alkyl-, alkenyl-, or alkynyl-containing groups (such as alkoxy, alkaryl, and alkamino) can be straight or branched chains and preferably have from one to five carbon atoms, more preferably from one to four carbon atoms, even more preferably from one to three carbon atoms, most preferably from one to two carbon atoms. As discussed above, the R substituents hereof can also contain amino functionalities, e.g. alkamino groups, which can be primary, secondary or tertiary amines or quaternary ammonium. These include mono-, di- and tri-alkylamino and alkoxyamino groups wherein the aliphatic portion chain length is preferably as described above. The R substituents can also be substituted with other groups, such as halogens (e.g. chloride, fluoride, and bromide), halogenated aliphatic or aryl groups, and hydroxy (e.g. hydroxy substituted aliphatic groups). Suitable halogenated R groups could include, for example, tri-halogenated (preferably fluoro) alkyl groups such as —$R^1$—$C(F)_3$, wherein $R^1$ is $C_1$–$C_3$ alkyl. Examples of such polysiloxanes include polymethyl-3,3,3 trifluoropropylsiloxane.

Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred. Other suitable R groups include methyl, methoxy, ethoxy, propoxy, and aryloxy. The three R groups on the end caps of the silicone may also represent the same or different groups.

The nonvolatile polyalkylsiloxane fluids that may be used include, for example, polydimethylsiloxanes. These siloxanes are available, for example, from the General Electric Company in their Viscasil R and SF 96 series, and from Dow Coming in their Dow Coming 200 series.

The polyalkylaryl siloxane fluids that may be used, also include, for example, polymethylphenylsiloxanes. These siloxanes are available, for example, from the General Electric Company as SF 1075 methyl phenyl fluid or from Dow Coming as 556 Cosmetic Grade Fluid.

The polyether siloxane copolymers that may be used include, for example, a polypropylene oxide modified polydimethylsiloxane (e.g., Dow Coming DC-1248) although ethylene oxide or mixtures of ethylene oxide and propylene oxide may also be used. The ethylene oxide and polypropylene oxide concentrations must be sufficiently low to prevent solubility in water and the composition hereof.

Suitable alkylamino substituted silicones include those which conform to the following structure (II)

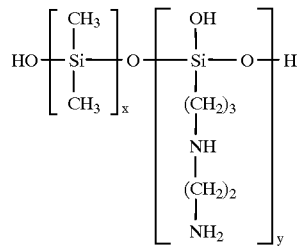

wherein x and y are integers. This polymer is also known as "amodimethicone".

Suitable cationic silicone fluids include those which conform to the formula (III) $(R_1)_a G_{3-a}$—Si—$(—OSiG_2)_n$—$(—OSiG_b(R_1)_{2-b})_m$—O—$SiG_{3-a}(R_1)_a$, wherein G is selected from the group consisting of hydrogen, phenyl, hydroxy, $C_1$–$C_8$ alkyl and preferably methyl; a is 0 or an integer having a value from 1 to 3, preferably 0; b is 0 or 1, preferably 1; the sum n+m is a number from 1 to 2,000 and preferably from 50 to 150, n being able to denote a number from 0 to 1,999 and preferably from 49 to 149 and m being able to denote an integer from 1 to 2,000 and preferably from 1 to 10; $R_1$ is a monovalent radical conforming to the formula $CqH_{2q}L$ in which q is an integer having a value of from 2 to 8 and L is selected from the following groups:

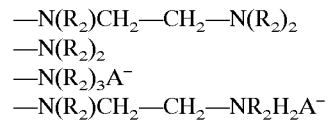

in which $R_2$ is selected from the group consisting of hydrogen, phenyl, benzyl, a saturated hydrocarbon radical, preferably an alkyl radical containing from 1 to 20 carbon atoms, and $A^-$ is a halide ion.

An especially preferred cationic silicone corresponding to formula (III) is the polymer known as "trimethylsilylamodimethicone", of formula (IV):

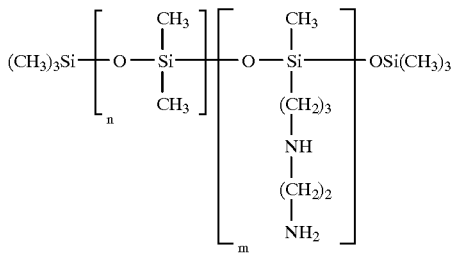

Other silicone cationic polymers which can be used in the shampoo compositions are represented by the formula (V):

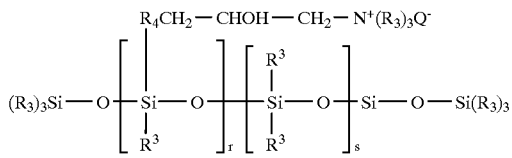

where $R^3$ denotes a monovalent hydrocarbon radical having from 1 to 18 carbon atoms, preferably an alkyl or alkenyl radical such as methyl; $R_4$ denotes a hydrocarbon radical, preferably a $C_1$–$C_{18}$ alkylene radical or a $C_1$–$C_{18}$, and more preferably $C_1$–$C_8$, alkyleneoxy radical; Q is a halide ion, preferably chloride; r denotes an average statistical value from 2 to 20, preferably from 2 to 8; s denotes an average statistical value from 20 to 200, and preferably from 20 to 50. A preferred polymer of this class is available from Union Carbide under the name "UCAR SILICONE ALE 56."

Other optional silicone fluids are the insoluble silicone gums. These gums are polyorganosiloxane materials having a viscosity at 25° C. of greater than or equal to 1,000,000 centistokes. Silicone gums are described in U.S. Pat. No. 4,152,416; Noll and Walter, *Chemistry and Technology of Silicones*, New York: Academic Press 1968; and in General Electric Silicone Rubber Product Data Sheets SE 30, SE 33, SE 54 and SE 76, all of which are incorporated herein by reference. The silicone gums will typically have a mass molecular weight in excess of about 200,000, generally between about 200,000 and about 1,000,000, specific examples of which include polydimethylsiloxane, (polydimethylsiloxane) (methylvinylsiloxane) copolymer, poly(dimethylsiloxane) (diphenyl siloxanexmethylvinylsiloxane) copolymer and mixtures thereof.

Another category of nonvolatile, insoluble silicone fluid conditioning agents are the high refractive index silicones, having a refractive index of at least about 1.46, preferably at least about 1.48, more preferably at least about 1.52, most preferably at least about 1.55. The refractive index of the polysiloxane fluid will generally be less than about 1.70, typically less than about 1.60. In this context, polysiloxane "fluid" includes oils as well as gums.

The high refractive index polysiloxane fluid includes those represented by general Formula (I) above, as well as cyclic polysiloxanes such as those represented by Formula (VI) below:

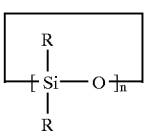

wherein R is as defined above, n is from about 3 to about 7, preferably from 3 to 5.

The high refractive index polysiloxane fluids contain a sufficient amount of aryl-containing R substituents to increase the refractive index to the desired level, which is described above. In addition, R and n must be selected so that the material is nonvolatile, as defined above.

Aryl-containing substituents contain alicyclic and heterocyclic five and six membered aryl rings, and substituents containing fused five or six membered rings. The aryl rings themselves can be substituted or unsubstituted. Substituents include aliphatic substituents, and can also include alkoxy substituents, acyl substituents, ketones, halogens (e.g., Cl and Br), amines, etc. Exemplary aryl-containing groups include substituted and unsubstituted arenes, such as phenyl, and phenyl derivatives such as phenyls with $C_1$–$C_5$ alkyl or alkenyl substituents, e.g., allylphenyl, methyl phenyl and ethyl phenyl, vinyl phenyls such as styrenyl, and phenyl alkynes (e.g. phenyl $C_2$–$C_4$ alkynes). Heterocyclic aryl groups include substituents derived from furan, imidazole, pyrrole, pyridine, etc. Fused aryl ring substituents include, for example, napthalene, coumarin, and purine.

In general, the high refractive index polysiloxane fluids will have a degree of aryl-containing substituents of at least about 15%, preferably at least about 20%, more preferably at least about 25%, even more preferably at least about 35%, most preferably at least about 50%. Typically, although it is not intended to necessarily limit the invention, the degree of aryl substitution will be less than about 90%, more generally less than about 85%, preferably from about 55% to about 80%.

The polysiloxane fluids are also characterized by relatively high surface tensions as a result of their aryl substitution. In general, the polysiloxane fluids hereof will have a surface tension of at least about 24 dynes/$cm^2$, typically at least about 27 dynes/$cm^2$. Surface tension, for purposes hereof, is measured by a de Nouy ring tensiometer according to Dow Corning Corporate Test Method CTM 0461, Nov. 23, 1971. Changes in surface tension can be measured according to the above test method or according to ASTM Method D 1331.

Preferred high refractive index polysiloxane fluids have a combination of phenyl or phenyl derivative substituents (preferably phenyl), with alkyl substituents, preferably $C_1$–$C_4$ alkyl (most preferably methyl), hydroxy, $C_1$–$C_4$ alkylamino (especially —$R^1NHR^2NH2$ where each $R^1$ and $R^2$ independently is a $C_1$–$C_3$ alkyl, alkenyl, and/or alkoxy. High refractive index polysiloxanes are available from Dow Coming Corporation (Midland, Mich., U.S.A.) Huls America (Piscataway, N.J., U.S.A.), and General Electric Silicones (Waterford, N.Y., U.S.A.).

References disclosing examples of some suitable silicone fluids for use in the shampoo compositions include U.S. Pat. Nos. 2,826,551, 3,964,500, 4,364,837, British Patent 849, 433, and *Silicon Compounds*, Petrarch Systems, Inc. (1984), all of which are incorporated herein by reference.

Silicone resins can be included in the silicone conditioning agent. These resins are highly crosslinked polymeric siloxane systems. The crosslinking is introduced through the incorporation of trifunctional and tetrafunctional silanes with monofunctional or difunctional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of crosslinking) such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinyl-chlorosilanes, and tetrachlorosilane, with the methyl-substituted silanes being most commonly utilized. Preferred resins are offered by General Electric as GE SS4230 and SS4267. Commercially available silicone resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art.

Background material on silicones including sections discussing silicone fluids, gums, and resins, as well as manufacture of silicones, can be found in Encyclopedia of Polymer Science and Engineering, Volume 15, Second Edition, pp 204–308, John Wiley & Sons, Inc., 1989, incorporated herein by reference.

Silicone materials and silicone resins in particular, can conveniently be identified according to a shorthand nomenclature system well known to those skilled in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$ and Q denotes the quadri- or tetra-functional unit $SiO_2$. Primes of the unit symbols, e.g., M', D', T', and Q' denote substituents other than methyl, and must be specifically defined for each occurrence. Typical alternate substituents include groups such as vinyl, phenyls, amines, hydroxyls, etc. The molar ratios of the various units, either in terms of subscripts to the symbols indicating the total number of each type of unit in the silicone (or an average thereof) or as specifically indicated ratios in combination with molecular weight complete the description of the silicone material under the MDTQ system. Higher relative molar amounts of T, Q, T' and/or Q' to D, D', M and/or M' in a silicone resin is indicative of higher levels of crosslinking. As discussed before, however, the overall level of crosslinking can also be indicated by the oxygen to silicon ratio.

The silicone resins for use herein which are preferred are MQ, MT, MTQ, MDT and MDTQ resins. Thus, the preferred silicone substituent is methyl. Especially preferred are MQ resins wherein the M:Q ratio is from about 0.5:1.0 to about 1.5:1.0 and the average molecular weight of the resin is from about 1000 to about 10,000.

The weight ratio of the nonvolatile silicone fluid, having refractive index below 1.46, to the silicone resin component, when used, is preferably from about 4:1 to about 400:1, preferably this ratio is from about 9:1 to about 200:1, more preferably from about 19:1 to about 100:1, particularly when the silicone fluid component is a polydimethylsiloxane fluid or a mixture of polydimethylsiloxane fluid and polydimethylsiloxane gum as described above. Insofar as the silicone resin forms a part of the same phase in the compositions hereof as the silicone fluid, i.e. the conditioning active, the sum of the fluid and resin should be included in determining the level of silicone conditioning agent in the composition.

Optional Agents

The shampoo compositions of the present invention may further comprise additional materials which improve the performance and/or aesthetics of the compositions of the present invention. These materials compete with other shampoo composition materials for solubilization by the surfactant component. As a result, they impact both the amount of coacervate which forms upon dilution and the composition of this coacervate. Additionally, the additional optional agents are also entrapped in the coacervate. The styling polymer/volatile carrier droplets are deposited onto the hair by the coacervate, thus these optional agents can be used to directly influence styling performance by impacting the amount of coacervate formed as well as hair feel by impacting the composition of the coacervate.

Highly preferred optional agents includes crystalline materials that can be categorized as acyl derivatives, long chain amine oxides, or combinations thereof, concentrations of which range from about 0.1% to about 5.0%, preferably from about 0.5% to about 3.0%, by weight of the shampoo compositions. These agents are described as suspending agents in U.S. Pat. No. 4,741,855, and U.S. Reissue Pat. No. 34,584 (Grote et al.), which descriptions are incorporated herein by reference. These preferred materials include ethylene glycol esters of fatty acids preferably having from about 16 to about 22 carbon atoms. More preferred are the ethylene glycol stearates, both mono and distearate, but particularly the distearate containing less than about 7% of the mono stearate. Other suitable optional agents include alkanol amides of fatty acids, preferably having from about 16 to about 22 carbon atoms, more preferably about 16 to 18 carbon atoms, preferred examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); glyceryl esters (e.g., glyceryl distearate) and long chain esters of long chain alkanol amides (e.g., stearamide diethanolamide distearate, stearamide monoethanolamide stearate). Long chain acyl derivatives, ethylene glycol esters of long chain carboxylic acids, long chain amine oxides, and alkanol amides of long chain carboxylic acids in addition to the preferred materials listed above may be used as suspending agents.

Other long chain acyl derivatives suitable for use as additional optional agents include N,N-dihydrocarbyl amido benzoic acid and soluble salts thereof (e.g., Na, K), particularly N,N-di(hydrogenated) $C_{16}$, $C_{18}$ and tallow amido benzoic acid species of this family, which are commercially available from Stepan Company (Northfield, Ill., USA).

Examples of suitable long chain amine oxides include alkyl ($C_{16}$–$C_{22}$) dimethyl amine oxides, e.g., stearyl dimethyl amine oxide.

Method of Use

The shampoo compositions of the present invention are used in a conventional manner for cleansing and styling hair.

An effective amount of the composition for cleansing and styling the hair is applied to the hair, that has preferably been wetted with water, and is then rinsed off. Such effective amounts generally range from about 1 gm to about 50 gm, preferably from about 1 gm to about 20 gm. Application to the hair typically includes working the composition through the hair such that most or all of the hair is contacted with the composition.

This method for cleansing and styling the hair comprises the steps of a) wetting the hair with water, b) applying an effective amount of the shampoo composition to the hair, c) shampooing the hair with the composition, and d) rinsing the composition from the hair with water. These steps can be repeated as many times as desired to achieve the cleansing and styling benefit desired. The method is preferably employed daily, every other day, or every third day, to provide and maintain the hair cleansing and styling performance described herein.

EXAMPLES

The styling shampoo compositions illustrated in Examples I–X illustrate specific embodiments of the shampoo compositions of the present invention, but are not intended to be limiting thereof. Other modifications can be undertaken by the skilled artisan without departing from the spirit and scope of this invention. These exemplified embodiments of the styling shampoo compositions of the present invention provide cleansing of hair and improved hair styling performance.

The shampoo compositions illustrated in Examples I–X are prepared by conventional formulation and mixing methods, an example of which is set forth hereinbelow. All exemplified amounts are listed as weight percents and exclude minor materials such as diluents, filler, and so forth, unless otherwise specified.

Preparation

The styling shampoo compositions of the present invention may be prepared using conventional formulation and mixing techniques. The hair styling polymer should first be dissolved in the volatile carrier. This styling polymer/volatile carrier premix may then be added to a premix of the surfactants, or some portion of the surfactants, and the solid components which has been heated to melt the solid components, e.g., about 87° C. This mixture is then pumped through a high shear mill and cooled, and then the remaining components are mixed in. Alternatively, the styling polymer/volatile carrier premix may be added to this final mix, after cooling. The composition should have a final viscosity of from about 2000 to about 12,000 cps. The viscosity of the composition can be adjusted using sodium chloride or ammonium xylenesulfonate as needed.

The styling polymer/volatile solvent premix, as exemplified in the following examples, may be a combination of styling polymers/solvent as described hereinbelow.

|  | w/w ratio |
|---|---|
| Mixture A. | |
| Styling Polymer: t-butyl acrylate/2-ethylhexyl methacrylate (90/10 w/w) | 40 |
| Volatile Solvent: isododecane | 60 |
| Mixture B. | |
| Styling Polymer: t-butyl acrylate/2-ethylhexyl methacrylate (90/10 w/w) | 50 |
| Volatile Solvent: isododecane | 50 |

-continued

|  | w/w ratio |
|---|---|
| Mixture C. | |
| Styling Polymer: t-butyl acrylate/2-ethylhexyl methacrylate/PDMS macromer (81/9/10 w/w) | 40 |
| Volatile Solvent: isododecane | 60 |

| | Weight % | | | | |
|---|---|---|---|---|---|
| Component | I | II | III | IV | V |
| Ammonium Laureth Sulfate | 9.0 | 9.0 | 9.0 | 9.0 | 9.0 |
| Ammonium Lauryl Sulfate | 3.0 | 3.0 | 3.0 | 3.0 | 3.0 |
| Lauroamphoacetate | 6.0 | 6.0 | 6.0 | 6.0 | 6.0 |
| Mixture A | — | 4.0 | 4.0 | 4.0 | — |
| Mixture B | 4.0 | — | — | — | 4.0 |
| Dihydrogenated Tallowamidoethyl Hydroxyethylmonium Methosulfate(1) | — | — | 1.0 | 1.0 | — |
| Ditallowamidoethyl Hydroxypropylmonium Methosulfate(2) | — | — | — | — | 1.0 |
| Citric Acid | 1.0 | 0.88 | 1.0 | 1.0 | 1.0 |
| Laureth 4 | 0.17 | 0.17 | 0.17 | 0.17 | 0.17 |
| Monosodium Phosphate | — | 0.1 | — | — | — |
| Disodium Phosphate | — | 0.2 | — | — | — |
| Glycol Distearate | 2.0 | 2.0 | 2.0 | 1.43 | 2.0 |
| Cocomonoethanol amide | 0.6 | 0.6 | 0.6 | 0.6 | 0.6 |
| Fragrance | 1.0 | 1.0 | 1.0 | 1.0 | 1.0 |
| Cetyl Alcohol | — | 0.42 | 0.42 | — | 0.42 |
| Trihydroxystearin | 0.05 | 0.25 | 0.15 | 0.15 | 0.15 |
| Polyquaternium 10 (JR30M) | 0.15 | — | — | — | 0.15 |
| Guar Hydroxypropyltrimonium Chloride(3) | 0.15 | 0.3 | 0.3 | 0.3 | 0.15 |
| Dimethicone | 0.25 | 0.5 | 0.25 | 1.0 | 0.25 |
| DMDM Hydantoin | 0.2 | 0.2 | 0.2 | 0.2 | 0.2 |
| Water | qs 100 | qs 100 | qs 100 | qs 100 | qs 100 |

(1)Available under the tradename Varisoft 110 from Sherex Chemical Co. (Dublin, Ohio, USA)
(2)Available under the tradename Varisoft 238 from Sherex Chemical Co. (Dublin, Ohio, USA)
(3)Available under the tradename Jaguar C-17 from Rhone-Poulenc. (Cranbury, New Jersey, USA)

| | Weight % | | | | |
|---|---|---|---|---|---|
| Component | VI | VII | VIII | IX | X |
| Ammonium Laureth Sulfate | 9.0 | 9.0 | 9.0 | 9.0 | 9.0 |
| Ammonium Lauryl Sulfate | 3.0 | 3.0 | 3.0 | 3.0 | 3.0 |
| Lauroamphoacetate | 6.0 | 6.0 | 6.0 | 6.0 | 6.0 |
| Mixture A | 4.0 | — | 4.0 | — | 4.0 |
| Mixture B | — | 4.0 | — | — | — |
| Mixture C | — | — | — | 4.0 | — |
| Dihydrogenated Tallowamidoethyl Hydroxyethylmonium Methosulfate(1) | 1.0 | 0.8 | — | 1.0 | 1.0 |
| PEG 14M | 0.3 | 0.15 | 0.3 | — | — |
| PEG 23M | — | — | — | 0.3 | 0.15 |
| Citric Acid | 1.0 | 1.0 | 1.0 | 1.0 | 1.0 |
| Laureth 4 | 0.17 | 0.17 | 0.17 | 0.17 | 0.17 |
| Glycol Distearate | 2.0 | 1.43 | 2.0 | 1.43 | 2.0 |
| Fragrance | 1.0 | 1.0 | 1.0 | 1.0 | 1.0 |
| Cetyl Alcohol | 0.42 | — | 0.42 | — | 0.42 |
| Trihydroxystearin | 0.15 | 0.05 | 0.25 | 0.15 | 0.15 |
| Polyquaternium 10 (JR30M) | 0.15 | — | 0.15 | — | 0.1 |
| Guar Hydroxypropyltrimonium Chloride(3) | 0.15 | 0.3 | 0.15 | 0.3 | 0.2 |
| Dimethicone | 0.25 | 0.25 | 1.0 | 0.25 | — |

-continued

| Component | VI | VII | VIII | IX | X |
|---|---|---|---|---|---|
| DMDM Hydantoin | 0.2 | 0.2 | 0.2 | 0.2 | 0.2 |
| Water | qs 100 | qs 100 | qs 100 | qs 100 | qs 100 |

(1)Available under the tradename Varisoft 110 from Sherex Chemical Co. (Dublin, Ohio, USA)
(3)Available under the tradename Jaguar C-17 from Rhone-Poulenc. (Cranbury, New Jersey, USA)

What is claimed is:

1. A styling shampoo composition comprising:
   (a) from about 5% to about 50% by weight of a detersive surfactant selected from the group consisting of anionic surfactants, zwitterionic and amphoteric surfactants, and combinations thereof;
   (b) from about 0.025% to about 3% by weight of an organic cationic deposition polymer which has a cationic charge density of from about 0.2 meq/gm to about 7 meq/gm and an average molecular weight of from about 5,000 to about 10 million selected from the group consisting of cationic cellulose derivatives, cationic starch derivatives, cationic guar derivatives and mixtures thereof;
   (c) from about 0.1% to about 10% by weight of a water-insoluble hair styling polymer selected from the group consisting of silicon grafted polymers, organic polymers comprising one or more polymerizable hydrophobic monomers, and mixtures thereof;
   (d) from about 0.1% to about 10% by weight of a volatile, water-insoluble carrier for the hair styling polymer selected from the group consisting of hydrocarbons, ethers, esters, amines, and alcohols;
   (e) from about 0.005% to about 2.0% by weight of a crystalline hydroxyl-containing stabilizing agent having the formula

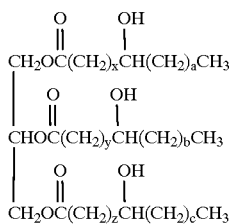

wherein: (x+a) is between 11 and 17, (y+b) is between 11 and 17, (z+c) is between 11 and 17; and
   (f) from about 25.0% to about 94.8% by weight water.

2. The composition of claim 1 wherein the detersive surfactant is selected from the group consisting of a combination of anionic and amphoteric surfactants, and a combination of anionic and zwitterionic surfactants.

3. The composition of claim 2 wherein the anionic surfactant is selected from the group consisting of ammonium lauryl sulfate, ammonium laureth sulfate, alkyl glyceryl ether sulfonate, and mixtures thereof; the amphoteric surfactant is selected from the group consisting of lauroamphoacetate, lauroamphodiacetate, cocoamphoacetate, cocoamphodiacetate, and mixture thereof; and the zwitterionic surfactant is a betaine surfactant.

4. The composition of claim 3 wherein the composition comprises from about 0.1% to about 0.25% by weight of the organic cationic deposition polymer having a cationic charge density of from about 0.6 meq/g to about 2.0 meq/g.

5. The composition of claim 4 wherein the cationic cellulose derivative is Polyquaternium-10 and the cationic guar derivative is guar hydroxypropyltrimonium chloride.

6. The composition of claim 1 wherein the composition comprises from about 0.5% to about 5% of the water-insoluble hair styling polymer.

7. The styling shampoo composition according to claim 6 wherein the polymerizable hydrophobic monomers are selected from the group consisting of acrylic or methacrylic acid esters of $C_1$–$C_{18}$ alcohols, styrene, polystyrene macromer, vinyl acetate, vinyl chloride, vinylidene chloride, vinyl propionate, alpha-methylstyrene, t-butylstyrene, butadiene, cyclohexadiene, ethylene, propylene, vinyl toluene, t-butyl ethacrylate, and mixtures thereof.

8. The composition of claim 7 wherein the water-insoluble hair styling polymer is an organic styling polymer selected from the group consisting of t-butyl acrylate/2-ethylhexyl acrylate copolymers having a weight/weight ratio of monomers of about 95/5, about 90/10, about 80/20, about 70/30, about 60/40, and about 50/50; t-butyl acrylate/2-ethylhexyl methacrylate copolymers having a weight/weight ratio of monomers of about 95/5, about 90/10, about 80/20, about 70/30, about 60/40, and about 50/50; t-butyl methacrylate/2-ethylhexyl acrylate copolymers having a weight/weight ratio of monomers of about 95/5, about 90/10, about 80/20, about 70/30, about 60/40, and about 50/50; t-butyl methacrylate/2-ethylhexyl methacrylate copolymers having a weight/weight ratio of monomers of about 95/5, about 90/10, about 80/20, about 70/30, about 60/40, and about 50/50; t-butyl ethacrylate/2-ethylhexyl methacrylate copolymers having a weight/weight ratio of monomers of about 95/5, about 90/10, about 80/20, about 70/30, about 60/40, and about 50/50; vinyl pyrrolidone/vinyl acetate copolymers having a weight/weight ratio of monomers of about 10/90, and about 5/95; and mixtures thereof.

9. A composition according to claim 4 which further comprises from about 0.05% to about 5% by weight of a non-polymeric, cationic spreading agent, that comprises from two to four N-radicals, wherein the N-radicals are substituted or unsubstituted carbon chains having from about 12 to about 30 carbon atoms.

10. A composition according to claim 1 which further comprises from about 0.025% to about 1.5% of a polyalkylene glycol, wherein said polyalkylene glycol is characterized by the general formula:

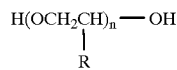

wherein R is hydrogen, methyl or mixtures thereof, and n is an integer having an average value of from about 1,500 to about 25,000.

11. The composition of claim 10 wherein the polyalkylene glycol is PEG-14 M or PEG-23M.

12. The composition of claim 1 wherein the crystalline hydroxyl-containing stabilizing agent is trihydroxystearin.

13. The composition of claim 1 wherein the water-insoluble hair styling polymer is a silicone grafted polymer selected from the group consisting of:
   (i) t-butylacrylatye/t-butyl-methacrylate/2-ethylhexyl-methacrylate/PDMS macromer—20,000 molecular weight macromer 31/27/32/10;
   (ii) t-butylmethacrylate/2-ethylhexyl-methacrylate/PDMS macromer—15,000 molecular weight macromer 75/10/15;

(iii) t-butylmethacrylate/2-ethylhexyl-acrylate/PDMS macromer—10,000 molecular weight macromer 65/15/20;

(iv) t-butylacrylate/2-ethylhexyl-acrylate/PDMS macromer—14,000 molecular weight macromer 77/11/12;

(v) t-butylacrylate/2-ethylhexyl-methacrylate/PDMS macromer—13,000 molecular weight macromer 81/9/10; and (vi) and mixtures thereof.

14. The composition of claim 1 wherein the composition comprises from about 1% to about 6% of the water-insoluble volatile carrier and wherein the water-insoluble carrier has a boiling point from about 100° C. to about 200° C.

15. The composition of claim 14 wherein the water-insoluble volatile carrier is selected from the group consisting of dodecane, isododecane, isotetradecane, isohexadecane, 2,5-dimethyldecane, diethyl succinate, dimethyl succinate, diethyl malonate, dimethyl malonate, and mixtures thereof.

16. The composition of claim 1 wherein the composition comprises a weight ratio of the water-insoluble hair styling polymer to the water-insoluble solvent of from about 30:70 to about 60:40.

17. The composition of claim 9 wherein the cationic spreading agent comprise a nonionic hydrophilic substituent.

18. The composition of claim 17 wherein the nonionic hydrophilic substituent is selected from the group consisting of alkoxy, polyoxalkylene, alkylamido, hydroxyalkyl, alkylester moieties, and mixtures thereof.

19. The composition of claim 18 wherein the cationic spreading agent is selected from the group consisting of ditallowdimethyl ammonium chloride, ditallowamidoethyl hydroxypropylmonium methosulfate, dihydrogenated tallowamidoethyl hydroxyethylmonium methosulfate, ditallowamidoethyl hydroxyethylmonium methosulfate, di(partially hardened soyoylethyl) hydroxyethylmonium methosulfate, and mixtures thereof.

20. The composition of claim 19 wherein the cationic spreading agent is dihydrogenated tallowamidoethyl hydroxyethylmonium methosulfate.

21. The composition of claim 9 wherein the composition comprises from about 0.2% to about 1% of the cationic spreading agent.

22. The composition of claim 1 wherein the composition further comprises a non-volatile silicone conditioning agent selected from the group consisting of polyarylsiloxanes, polyalkyl siloxanes, polyalkylarylsiloxanes, derivatives thereof, and mixtures thereof.

23. The composition of claim 22 wherein the composition comprises from about 0.1% to about 3% by weight of a non-volatile polydimethylsiloxane conditioning agent.

24. The composition according to claim 9 which further comprises from about 0.025% to about 1.5% of a polyalkylene glycol, wherein said polyalkylene glycol is characterized by the general formula:

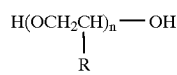

wherein R is hydrogen, methyl or mixtures thereof, and n is an integer having an average value of from about 1,500 to about 25,000.

25. The composition of claim 24 wherein the composition further comprises a non-volatile silicone conditioning agent selected from the group consisting of polyarylsiloxanes, polyalkyl siloxanes, polyalkylarylsiloxanes, derivatives thereof, and mixtures thereof.

26. The composition of claim 10 wherein the composition further comprises a non-volatile silicone conditioning agent selected from the group consisting of polyarylsiloxanes, polyalkyl siloxanes, polyalkylarylsiloxanes, derivatives thereof, and mixtures thereof.

27. The composition of claim 1 wherein the composition further comprises from about 0.1% to about 5% of an ethylene glycol stearate.

28. The styling shampoo composition according to claim 7 the polymerizable hydrophobic monomers is selected from the group consisting of n-butyl methacrylate, isobutyl methacrylate, t-butyl acrylate, t-butyl methacrylate, t-butyl ethacrylate, 2-ethylhexyl methacrylate, methyl methacrylate, vinyl acetate, and mixtures thereof.

* * * * *